United States Patent [19]

Byers, Jr. et al.

[11] Patent Number: 4,838,705
[45] Date of Patent: Jun. 13, 1989

[54] APPARATUS FOR DETERMINING PERCENT OF MOISTURE

[75] Inventors: Charles H. Byers, Jr., Phoenix; Terry L. Michl, Scottsdale; Dennis E. Acord, Phoenix, all of Ariz.

[73] Assignee: Arizona Instrument Corporation, Tempe, Ariz.

[21] Appl. No.: 59,112

[22] Filed: Jun. 8, 1987

[51] Int. Cl.$^4$ .................. G01G 19/00; G01N 22/04
[52] U.S. Cl. ........................................ 374/14; 73/76; 177/25.14
[58] Field of Search ............... 73/76, 25; 177/245, 177/25.14; 374/14

[56] References Cited

U.S. PATENT DOCUMENTS

| | | | |
|---|---|---|---|
| 676,858 | 6/1901 | Arndt | 73/30 |
| 3,493,063 | 2/1970 | Bowers | 177/245 X |
| 3,909,598 | 9/1975 | Collins et al. | 73/76 X |
| 4,050,995 | 9/1977 | Bredeweg | 73/76 X |
| 4,554,132 | 11/1985 | Collins | 73/76 X |

OTHER PUBLICATIONS

"A Semiautomatic Electromagnetic Balance ... Moisture in Cellulose", by K. A. Lincoln, 12/2/58, U.S. Naval Radiological Defence Lab., Report, USNRDL TR-287, 23 pages.

Primary Examiner—Daniel M. Yasich
Attorney, Agent, or Firm—Cahill, Sutton & Thomas

[57] ABSTRACT

The apparatus determines the content by weight of a volatile fluid, such as water, in a sample under test where the volatile fluid is typically less than one-half percent by weight by heating the sample in a sealed chamber to evaporate the volatile fluid under test. The evaporated fluid is passed through a collector which senses and collects only the evaporated volatile fluid of interest which collection correspondingly increases the weight of the collector. Measuring the weight change of the collector and comparing it with the initial weight of the test sample provides a determination of the percent of the sensed volatile fluid in the test sample.

45 Claims, 3 Drawing Sheets

APPARATUS FOR DETERMINING PERCENT OF MOISTURE

BACKGROUND OF THE INVENTION

1. Field of the Invention

The present invention relates to apparatus for determining by weight the actual or proportional amount of a volatile fluid in a test sample and, more particularly, to apparatus for evaporating, collecting and weighing a volatile fluid of interest contained in the sample under test.

2. Description of Related Art

Various devices have been developed for determining the quantity, usually by weight, of a volatile fluid present within a test sample. Such determinations are important for quality control in manufacturing and, in some cases, required by law. One technique, known as loss on drying, for determining and measuring the amount of volatile fluid within a sample under test is described in U.S. Pat. No. 4,165,633. Therein is described apparatus for heating a test sample at a temperature of interest in view of the volatile fluid(s) to be measured. The change in weight of the sample prior to, during and subsequent to evaporation of the volatile fluid(s) of interest provides data for computing the percent by weight of the volatile fluid of interest in the test sample. Various computational techniques are employed to forecast the percentage determination based upon the initial weight loss rate. Such computational approximations reduce the time required to complete a test without serious derogation of the accuracy of the determination. Generally, loss on drying techniques are limited to approximately 0.1% minimum moisture loss due to secondary effects such as convective air currents, buoyancy effects and temperature gradients.

Various other sensors are presently in use to measure the quantity of volatile fluid in a gas stream. Of these types, infrared and capacitive sensors are capable of providing instantaneous measurements of the concentration of volatile fluid of interest in a gas stream passing through the sensor. To determine the amount of volatile fluid by weight, the readings provided by these sensors would have to be integrated over the time period of the test in order to obtain an approximation of sufficient accuracy to be useful in a variety of circumstances and to satisfy the differing criteria of various industries. Other problems such as preexisting moisture levels, transient response times and contamination which may be present in these types of sensors must be addressed. Another process is known as Karl Fischer analysis, uses toxic and cumbersome wet chemistry and amperommetry.

SUMMARY OF THE INVENTION

The present invention is directed to apparatus for collecting and weighing a volatile fluid present within a test sample. To obtain the volatile fluid of interest, such as water, the test sample is heated within a sealed chamber to evaporate the volatile fluid of interest. The gaseous form of the volatile fluid of interest is passed through a collector sensitive to the volatile fluid of interest which collector increases in weight in response to the volatile fluid of interest collected. A weight sensor supporting the collector provides an indication of the initial weight, interim weight and final weight of the collector during operation of the apparatus. Computational circuitry performs various calculations to provide an operator with a predictive and actual determination of the percent by weight of the volatile fluid of interest in the test sample.

It is therefore a primary object of the present invention to provide apparatus for collecting and weighing a specific volatile fluid contained in a sample under test.

Another object of the present invention is to provide apparatus for determining the moisture content in a range of one-half percent by weight or less of a sample under test.

Still another object of the present invention is to provide apparatus for heating a sample under test within a purged environment to collect, in gaseous form, a volatile fluid of interest contained in the sample.

Yet another object of the present invention is to provide apparatus using dry chemistry and gravimetry to obtain a relatively rapid determination of the moisture content in a sample under test.

A further object of the preset invention is to provide a moisture content analyzer usable in conjunction with a production line.

A still further object of the present invention is to provide a method for determining the percentage by weight of moisture in a sample under test.

A yet further object of the present invention is to provide a method using dry chemistry and gravimetry for collecting and weighing the moisture in a sample under test.

These and other objects of the present invention will become apparent to those skilled in the art as the description thereof proceeds.

DESCRIPTION OF THE PREFERRED EMBODIMENT

Various manufacturing processes, chemical reactions and laws attendant certain industries require that the percentage by weight of certain volatile fluids of interest present within a product be known. Various techniques have been developed to provide such information. There exists vacuum ovens and convention ovens which heat a test sample of the product to a temperature commensurate with the volatile fluid of interest to cause evaporation of such fluid. The resulting reduction in weight of the test sample provides an indication of the percentage by weight of the volatile fluid(s) which have evaporated; devices of this type are often referred to as loss on drying analyzers. Chemical analysis is also possible for certain volatile fluids of interest, such as water, through a process known as the Karl Fischer analysis. These chemical analysis methods, rely on the use of various reagents which may be toxic. Moreover, the chemical analysis methods usually require very skilled operators and are often quite time consuming.

Figure 1:
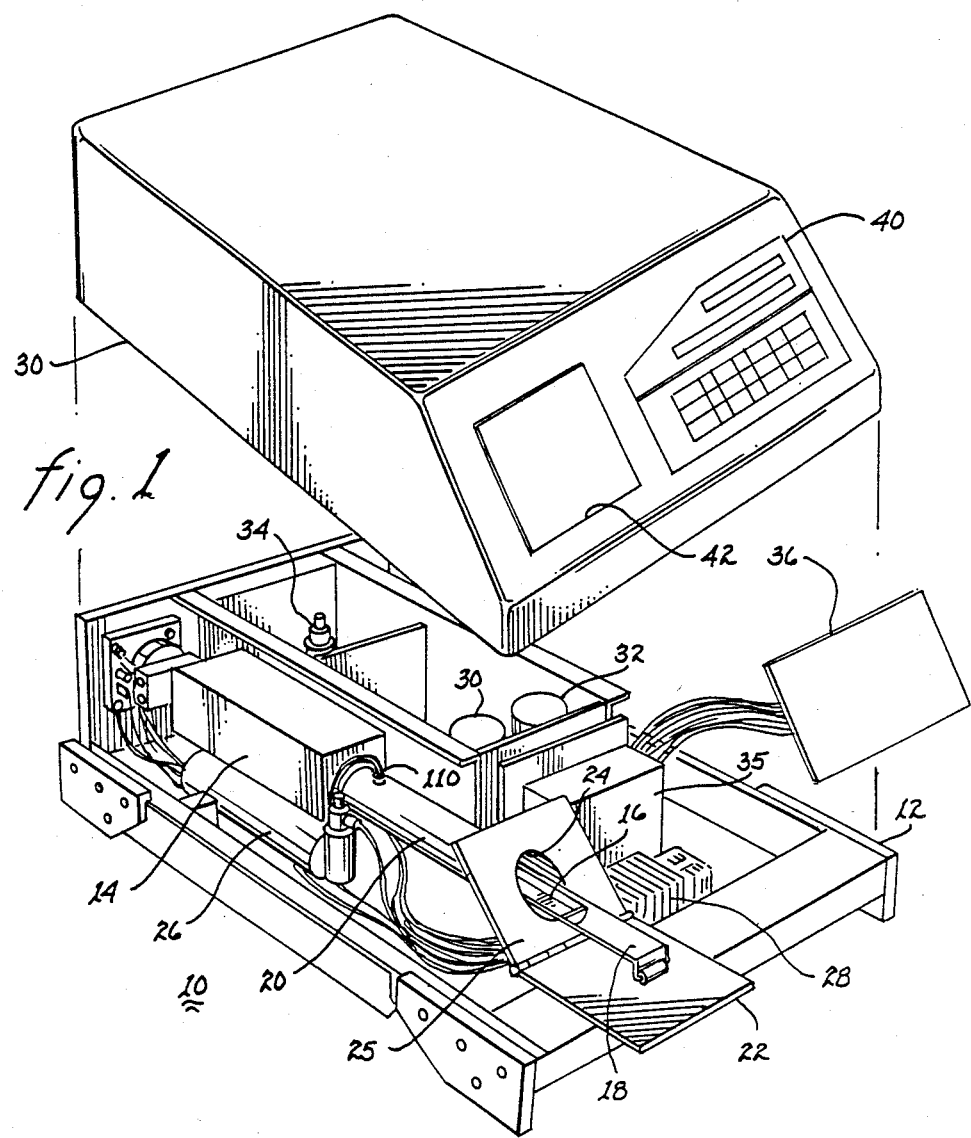
FIG. 1 is an exploded view illustrating apparatus for collecting and weighing a volatile fluid present within a test sample.
Figure 2:
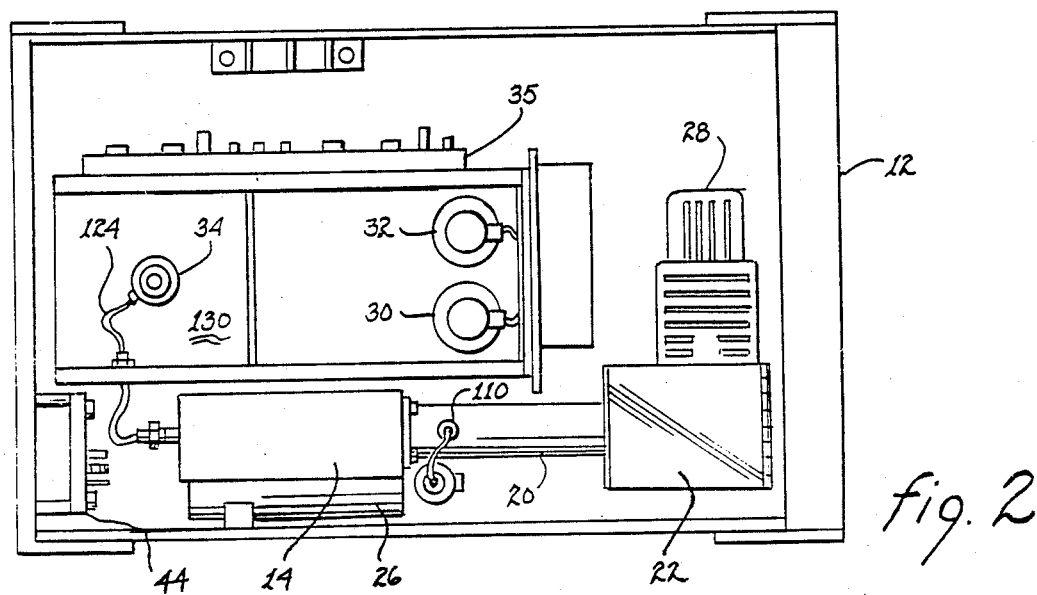
FIG. 2 is a top view of the major components illustrated in FIG. 1.

Referring to FIGS. 1 and 2, there is shown a moisture analyzer 10 for evaporating the moisture, water, present within a test sample. The evaporated moisture is collected in a collector which will collect all water introduced therein and pass other volatile fluids therethrough. A weight monitor determines the increase in weight of the collector in response to the water collected. The fluid flow path to the collector is selected to eliminate any weight variation due to repositioning of the fluid flow path during the collection period. Computational circuitry reacts with the weight monitor to provide an indication, real and forecast, of the weight of the moisture collected in absolute terms and as a percentage by weight of the sample tested.

More specifically, moisture analyzer 10 includes a chassis 12 having a compartment 14 within which the sample to be tested is heated. The sample may range in weight from 0.25 to 40 grams, depending upon the expected moisture content, to produce approximately 20 mg of water. A boat 16, supported upon a dolly 18, delivers the sample to be tested to compartment 14 through a delivery tube 20. When slurries or other non solid samples are to be tested, glass fiber filter paper may be used as a carrier for the sample. The delivery tube, in combination with compartment 14, defines an air tight enclosure upon closing of door 22 across entry way 24 in panel 25 of delivery tube 20. A pneumatically actuated plunger extends from within cylinder 26 for transporting by means of a magnetic connection dolly 18 to locate boat 16 into and out of compartment 14.

An air pump 28 delivers air under pressure to cylinder 26. In addition, it delivers a flow of air serially to containers 30, 32. These containers include a composition or structure for removing essentially any and all traces of the volatile fluid of interest. If water is the volatile fluid of interest, a desiccant is lodged within the two containers 30, 32 to dry the air. The desiccant may be silica gel, calcium sulphate or other compositions. Alternatively, a molecular sieve may be used. By means of appropriate flow control devices, air from containers 30, 32 may be used initially to purge compartment delivery tube 20 and compartment 14 of the volatile fluid of interest. Or, dry nitrogen gas may be used for such purging. In many test situations the initial step of purging is not necessary.

The sample, transported into compartment 14, is heated to a predetermined temperature, depending upon the characteristics of both the sample and the volatile fluid of interest, to evaporate the volatile fluid of interest. A flow of gas, dry nitrogen or dry air from containers 30, 32 in the event water is the volatile fluid of interest, is established through compartment 14 to transport the evaporated volatile fluid of interest to a collector 34. The collector reacts with the volatile fluid of interest to retain essentially all traces thereof and exhaust the remaining gases. A weight monitor 130, such as an electromagnetic force restoration balance, supports collector 34 and determines the amount of change in weight of the collector as a function of the volatile fluid of interest collected.

Controls for the various sequential steps, flow rates, and computations are performed by electronics representatively illustrated by printed circuit boards 35 and 36. This circuitry includes microcomputers, EPROM, EEPROM, RAM, 16 bit analog to digital converter and control circuitry. A cover 38 extends over chassis 12 and it's components to protect the equipment and yet provide access for an operator to perform the various manual functions necessary. The cover may be hinged along the rear bottom edge to chassis 12. Furthermore, the cover includes a display 40 representative of the state of operation of moisture analyzer 10, the results achieved and various instructions or cues for an operator. A control panel keyboard is also included. Hinged cover 22 is exposed through aperture 42 in cover 38 to facilitate insertion and withdrawal of boat 16 or samples placed therein. Suitable connecting devices 44 for connecting the moisture analyzer to a source of electrical power are provided. Additional electrical connections may be incorporated for interconnecting: a balance for weighing the sample and providing circuitry 35, 36 with a representative indication; a printer for printing the results achieved; and an external computer or logging device.

Figure 3:
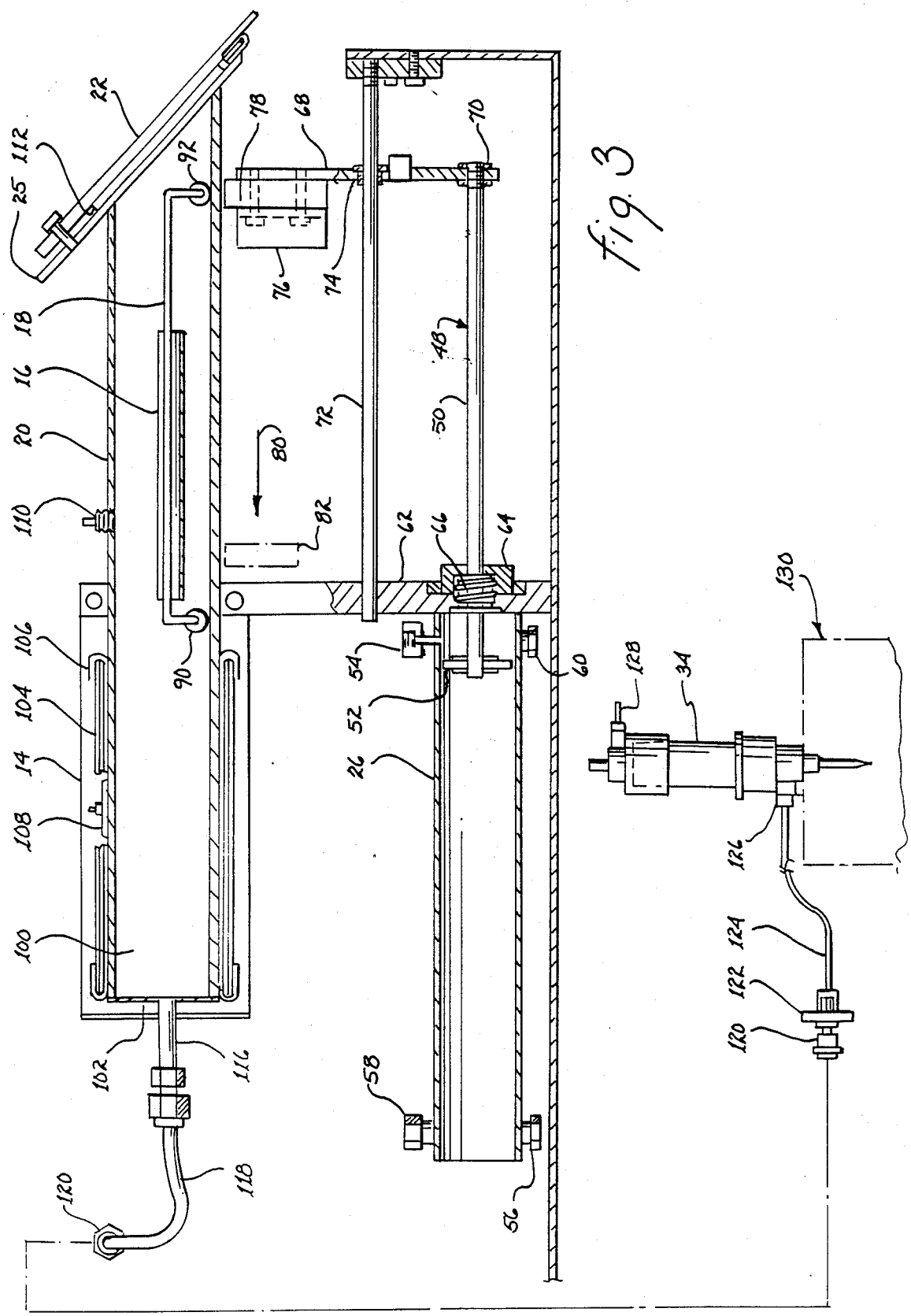
FIG. 3 is a partial cross sectional view illustrating the delivery system of the test sample and the collection system for a volatile fluid to be collected.

Referring particularly to FIG. 3, there is illustrated the operative elements attendant delivery of boat 16 containing a sample into compartment 14 and the air flows associated with such movement to deliver the volatile fluid in gaseous form to collector 34. Pneumatic cylinder 26 includes a plunger 48 having a piston 52 disposed within the cylinder. An inlet, such as fitting 54 conveys a source of air under pressure to the right side of piston 52. An exhaust port, such as exhaust fitting 56, accommodates air flow out of cylinder 26 on the left side of piston 52. A further inlet port, such as inlet fitting 58 conveys air under pressure into cylinder 26 on the left side of piston 52 and an exhaust port, such as exhaust fitting 60, permits discharge of air on the right side of piston 52. With appropriate valving, the exhaust ports cooperate with the respective inlet ports to effect movement of piston 52 within cylinder 26. In example, an air flow through inlet fitting 54 will create a pressure on the right side of piston 52, which pressure will force the piston to the left; back pressure is avoided by air flow exhausting through exhaust fitting 56. Movement of piston 52 to the left will draw plunger 48 therewith. An air flow through inlet fitting 58 will create a pressure on the left side of piston 52 to urge movement of the piston to the right; back pressure is avoided by exhausting the air on the right side of piston 52 through exhaust fitting 60. Accordingly, movement of piston 52 may be controlled by air inflow through one of inlet fittings 54, 58.

Figure 4:
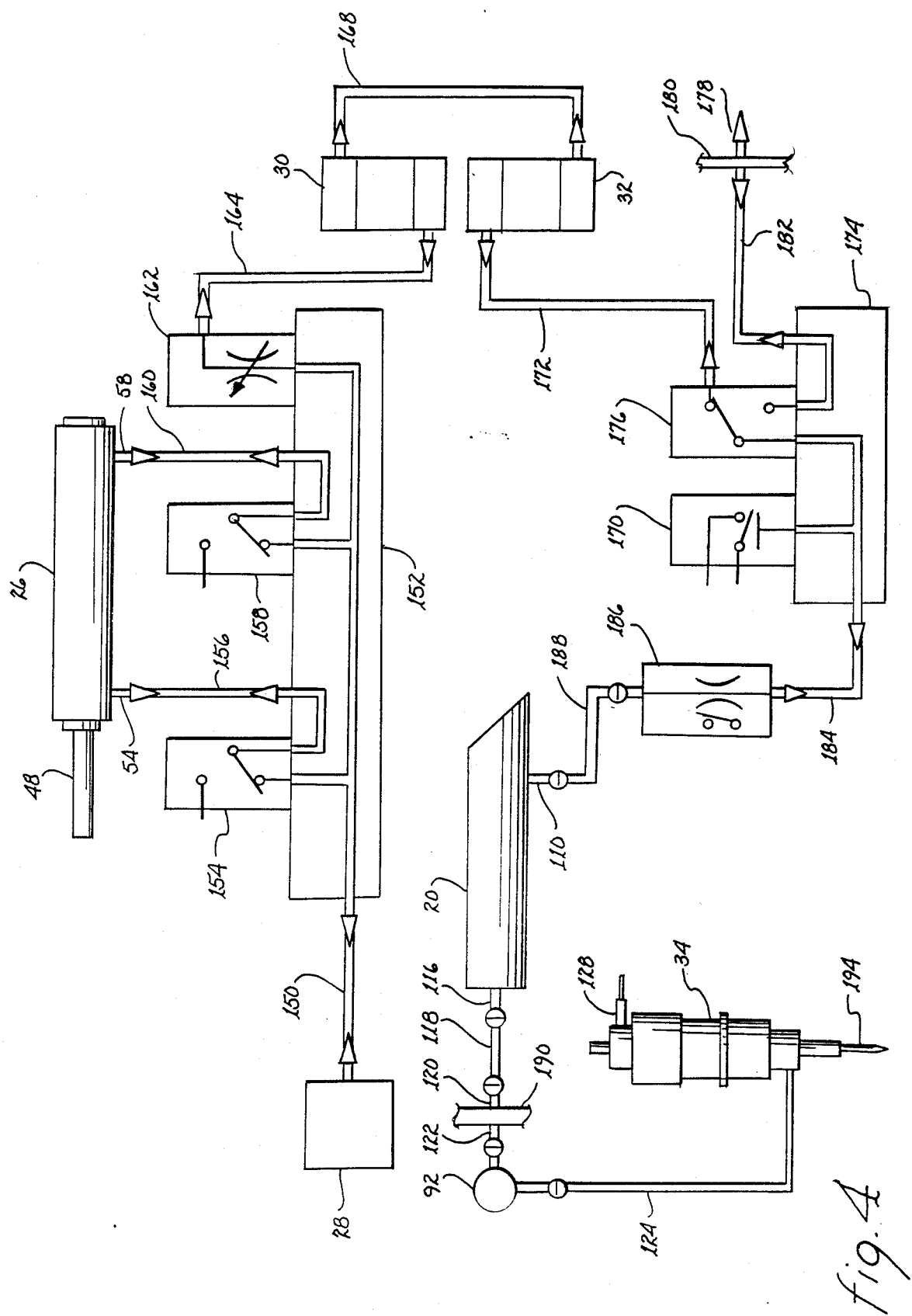
FIG. 4 illustrates a schematic of the pneumatic system attendant the apparatus shown in FIG. 1.

It is to be understood that the air inflows and outflows with respect to cylinder 26 may be controlled by solenoid operated valves, such as the type schematically shown in FIG. 4, as is well known to those skilled in the art.

Shaft 50 of plunger 48 is journaled in bulkhead 62 by journal member 64. Packing 66 or other air sealing means may be employed to prevent air flow from within cylinder 26 along shaft 50. A frame 68 is attached to shaft 50 by a attachment means 70. The frame may be journaled upon rod 72 to receive support and alignment through journal means 74. The rod is secured intermediate chassis 12 and bulkhead 62. Frame 68 includes a bracket 76 for securing a magnet 78 thereto. In response to rectilinear translation of shaft 50 to the left, magnet 78 will be repositioned in the direction indicated by arrow 80 to the position of the magnet indicated by dashed line 82.

Dolly 18 is supported upon front and rear rollers 90, 92. These rollers bear against the lower interior surface of delivery tube 20 to provide rolling support for the dolly and boat 16 supported thereon. The dolly is of non-magnetic material but roller 92 is of magnetically responsive material. Accordingly, magnet 78 will attract roller 92 to cause the roller to be repositioned commensurate with any change in position of the magnet. Movement of the magnet in a direction of arrow 80 will produce a commensurate movement of tray 16 into compartment 14 through the magnetic attraction of holder 92 to the magnet. Likewise, movement of the magnet in the opposite direction will withdraw dolly 18 from within the compartment. It may therefore be appreciated that movement of tray 16 can be effected without the risk of gas leakage from within delivery tube 20 resulting from use of mechanical components penetrably associated with the delivery tube or compartment 14 to relocate dolly 18.

Compartment 14 includes a chamber 100 which is defined by an extension of delivery tube 20 and having a bulkhead 102 at one end. A heating element 104, disposed in and retained by element 106, extends about compartment 100 to heat the compartment to a predetermined temperature at a predetermined rate. A heat sensor 108 is attached to the wall of compartment 100 to provide an indication of the temperature within the compartment.

An inlet fitting 110 may be disposed in delivery tube 20 to provide an air (or other gas) inflow into the delivery tube and compartment 100. It may be noted that door 22 in combination with gasket 112 and panel 25 defining entry way 24 provides a seal at the entrance to the delivery tube. A latch may also be employed. Outlet tube 116 exhausts the air (or gas) within compartment 100 to provide an air flow therethrough in combination with an inflow through inlet fitting 110. A conduit 118 conveys the exhausted air (gas) to a fitting 120. This fitting may include a quick disconnect 122 attached to a length of flexible tubing 124. This tubing is in communication with the interior of collector 34 through a further fitting 126. The collector includes an outlet port 128 for exhausting any air (gas) flowing through the collector. The collector 34 is supported upon an electromagnetic force restoration balance 130. Any increase in weight of the collector due to an accumulation of volatile fluid of interest emanating from the sample within compartment 100 would be registered by the balance.

The basic operation of the electromagnetic force restoration balance is one of restoring the balance to it's original position after having been deflected by an increase in weight of the item resting thereupon. Although minute, a resulting vertical motion of collector 34 results. Such motion, and the resulting repositioning of the collector with respect to the fixed position of fitting 122, may result in inaccurate readings due to the potentially variable force exerted by flexing of tubing 124 and acting upon the electromagnetic force restoration balance. Any such changes in apparent weight of the tubing would severely detract from the integrity and accuracy of the weight readings obtained. By employing a length of tubing 124 which is made of essentially perfectly elastic material, the change in position of collector 34 with respect to fitting 122 will have or produce no change in apparent weight of the tubing that can be sensed by the electromagnetic force balance. Accordingly, since the actual and apparent weight of tubing 124 remains constant, it, as well as the weight of collector 34, can be eliminated from the computations to be performed in determining the amount of volatile fluids collected.

A tubing of particular use as tubing 124 is made by the Dow Corning Company and sold under the mark "SILASTIC". One configuration of this tubing used with great success is tubing having an inside diameter of 0.058 inches and a wall thickness of 0.009 inches. Using this tubing, no noticeable errors were apparent even with measurements in the range of 1 mg. It is therefore critical that tubing 124 or other means for conveying the flow of air (gas) from a fixed location of moisture analyzer 10 to the vertically positionable collector must permit freedom of vertical movement of the collector without adding any forces in the vertical axis to the electromagnetic force restoration balance. Otherwise, severe limits on the minimum weights measurable with a sufficient degree of accuracy would be imposed.

In the present form of the invention, the moisture analyzer is used primarily for the purpose of determining the content of moisture, water, in a sample under test. The following description relating to FIG. 4 will be made with this consideration. It is to be noted that other volatile fluids might also be collected with appropriate changes or modifications to the air flow purifying apparatus and the collection apparatus for such volatile fluids.

Air pump 28 illustrated in FIG. 4 provides a source of air flow through a conduit 150 to a manifold 152. A solenoid operated valve 154 directs air through conduit 156 to inlet fitting 54 of air cylinder 26. As stated above, inflow of air through inlet fitting 54 will result in retraction of plunger 48 and bring about transport of tray 16 upon dolly 18 into chamber 100. A further solenoid operated valve 158 conveys a flow of air to conduit 160, which conduit is in fluid communication with inlet fitting 58. Flow of air through inlet fitting 58 will bring about extension of plunger 48 and withdrawal of tray 16 upon dolly 18 from chamber 100.

A needle valve, or restrictor, 162 regulates the air flow rate into conduit 164. Assuming that the volatile fluid to be measured is water, container 30 includes a charge of desiccant for the purpose of removing moisture from the air flowing into the container. A conduit 168 conveys air from container 30, which air has been fully or partially dried by the desiccant within the container. The at least partially dried air is conveyed to a second container 32 which also includes a charge of desiccant. This further charge of desiccant will remove essentially all of any remaining water in the air flowing into the container. It will be appreciated that the air flow rate, set by needle valve or restrictor 162, is a function of the size of the charge of the desiccant in one or both of containers 30, 32 and the preferable air flow rate through chamber 100 and collector 34. The essentially dry air is conveyed from container 21 through conduit 172 to manifold 174 via a solenoid operated valve 176. The valve controls whether the inflowing air is received from containers 30, 32 or received via conduit 182 from port 178 attached to a bulkhead 180 of the moisture analyzer. The dry air inflowing through conduit 172 can be channeled by valve 176 into conduit 184 and to a flow switch 186; a pressure switch 170 may be incorporated to ensure that the air pressure in conduit 184 is within acceptable limits. The dried air flows from the flow switch through conduit 188 to inlet fitting 110 located in the wall of delivery tube 20. The interior of the delivery tube is sealed during operation, as discussed above, and any air flowing thereinto is exhausted through outlet fitting 116 into conduit 118. Fittings 120, 122 convey the exhausted air through a bulkhead 190 of the moisture analyzer. Collector 34 receives the air inflowing from tubing 124. It includes a desiccator to remove the water from the inflowing air. The dry air is vented through exhaust port 128. A prong 194 extends downwardly from collector 34. This prong engages a commensurately configured cavity within the electromagnetic force restoration balance. By experiment, it has been determined that more accurate results are achieved by having a vertically upward flow through collector 34 than a horizontal flow therethrough.

During heating of the sample within compartment 100, particulate matter of the sample may be inadvertently conveyed by the air exhausted therefrom. Such particulate matter might jeopardize the integrity and accuracy of analysis of the moisture in the sample under test. To eliminate such particulate matter, a filter 192 may be employed to filter the air flowing into tubing 124.

In operation, any moisture within delivery tube 20 and chamber 100 or in any conduits or other air flow passageways associated therewith may be initially removed by passing a quantity of air dried by the desiccants in containers 30, 32 through the system. Any change in weight noted in collector 34 will represent the moisture present in the air flow system. A lack of further increase in weight or significant reduction in rate of weight increase will indicate that all moisture has been removed. By experimentation, it has been found that a collector 34 of the type presently used can contain approximately 2 grams of water before it becomes ineffective. Generally, such collection capability permits approximately 100 tests under normal conditions of expecting a 20 mg water collection per test. Thus, the slight increase in weight which may result during purging of the apparatus is of little moment in affecting the water collection and retention capability of the collector.

It is to be noted that initial purging may not always be necessary. After the pneumatic system has been purged of moisture if such initial purging is performed, a sample is placed upon boat 16 and panel 22 is closed to seal the delivery tube. Upon actuation of solenoid 154, piston 52 will be rectilinearly translated to produce a commensurate repositioning of magnet 78. Movement of the magnet will exert a force upon roller 92 of dolly 18 to roll tray 16 into chamber 100. On energization of heater 104 to a predetermined temperature, as regulated by sensor 108 and circuitry associated therewith, the water within the sample will be evaporated. Dry air inflow (or dry nitrogen) through inlet 110 will become moisture laden by the evaporated water. The moisture laden air (nitrogen) is exhausted through conduit 116 and conveyed to collector 34. The desiccant within the collector will withdraw all water from the air (nitrogen) flowing therethrough. The accumulation of water will increase the weight of the collector which weight increase is sensed by electromagnetic force restoration balance 130. As stated above, the characteristics of tubing 124 are such that it's weight, both actual and apparent, remains essentially constant during water accumulation within the collector and the resulting slight vertical oscillation of the collector; thereby, the flexible interconnection between the moving collector and the fixed source of the moisture laden air (nitrogen) will not affect the integrity of the electromagnetic force restoration balance to sense the weight of accumulating water within the collector.

Necessarily, various limit switches and other structural, mechanical and electrical details are necessary to provide an essentially automated operation as described above. As these elements are well known to those skilled in the art, details thereof have not been included.

The computations to be performed based upon the output signals provided by the electromagnetic force restoration balance are determined by proprietary circuitry. However, the circuitry for simply determining and converting an output signal from any one of many commercially available electromagnetic force restoration balances, such as one manufactured by Scientech, Inc., is circuitry well known to those skilled in the art.

In summary, the present invention includes three subsystems: (1) a control system for controlling the test sequence, performing the necessary calculations, keeping track of the timed functions and controlling the information display; (2) a sample pyrolysis system for moving the sample in and out of the oven, controlling the flow of dry gas over the sample and maintaining the oven temperature; and (3) a gas analysis system for removing the moisture vapor (volatile gas of interest) from the volatile gases driven from the sample in the pyrolysis system and converting the moisture to an electronic weight change value for processing by the control system.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. Apparatus for collecting and weighing a volatile fluid of interest from a sample under test, said apparatus comprising in combination:
   (a) an oven for heating the sample under test and converting the volatile fluid of interest to a gaseous state;
   (b) a collector for collecting the volatile fluid of interest, said collector increasing in weight during accretion of the volatile fluid of interest;
   (c) means for conveying flow of the volatile fluid of interest from said oven to said collector; and
   (d) means for determining the change in weight of said collector in response to collection of the volatile fluid of interest and during flow of the volatile fluid of interest into said collector, said weight change determining means including means for supporting said collector, means for accommodating repetitively downward movement of said supporting means from an initial position in response to the increase in weight of said collector and means for repetitively repositioning said collector to the initial position after each downward movement; and
   (e) means for interconnecting said conveying means with said collector, said interconnecting means including a length of flexible tubing which accommodates repositioning of said collector relative to said conveying means without imposing any changes in forces acting upon said collector due to any flexing of said tubing.

2. The apparatus as set forth in claim 1 wherein said oven includes a chamber for receiving and heating the sample and means for transporting the sample into and out of said chamber.

3. The apparatus as set forth in claim 2 including means for precluding free flow of the surrounding medium into and out of said oven.

4. The apparatus as set forth in claim 3 including means for urging the volatile fluid of interest from said oven to said collector.

5. The apparatus as set forth in claim 4 wherein said urging means includes means for pumping a gas into said oven.

6. The apparatus set forth in claim 2 wherein said transporting means includes a magnet, means for repositioning said magnet and means responsive to the magnetic field of said magnet for relocating the sample in response to the repositioned magnetic field resulting from repositioning of said magnet.

7. The apparatus as set forth in claim 1 wherein said determining means comprises an electromagnetic force restoration balance.

8. The apparatus as set forth in claim 7 wherein said balance repetitively repositions said collector during weight accretion and wherein said tubing isolates said collector from said conveying means to eliminate any apparent weight change of said collector that would otherwise be imposed by forces associated with said conveying means due to relative movement between said collector and said conveying means.

9. The apparatus as set forth in claim 1 wherein said conveying means includes a source of gas flow, conduit means for conveying a flow of gas from said source to said oven and means for eliminating any volatile fluid of interest from the gas flowing into said oven.

10. The apparatus as set forth in claim 9 wherein the volatile fluid of interest is water and wherein said eliminating means includes at least one container of desiccant.

11. The apparatus as set forth in claim 10 wherein said collector includes a charge of desiccant.

12. The apparatus as set forth in claim 1 wherein said balance repetitively repositions said collector during weight accretion and wherein said tubing isolates said collector from said conveying means to eliminate any apparent weight change of said collector that would otherwise be imposed by forces associated with said conveying means due to relative movement between said collector and said conveying means.

13. The apparatus as set forth in claim 12 wherein said isolating means includes a length of flexible tubing for conveying the volatile fluid of interest from a fixed location of said apparatus to said collector.

14. The apparatus as set forth in claim 1 wherein said oven includes a chamber for receiving and heating the sample and means for transporting the sample into and out of said chamber.

15. The apparatus as set forth in claim 14 wherein said transporting means includes a magnet, means for repositioning said magnet and means responsive to the magnetic field of said magnet for relocating the sample in response to the repositioned magnetic field resulting from repositioning of said magnet.

16. Apparatus for collecting and simultaneously weighing a volatile fluid of interest from a sample under test, said apparatus comprising in combination:
(a) an oven for heating the sample under test and converting the volatile fluid of interest to a gaseous state;
(b) a collector for collecting only the volatile fluid of interest;
(c) means for conveying flow of the volatile fluid of interest from said oven to said collector and said conveying means including a length of flexible tubing for conveying the volatile fluid of interest from a fixed location of said apparatus to said collector; and
(d) an electromagnetic force restoration balance for determining the change in weight of said collector in response to collection of the volatile fluid of interest by repetitively repositioning a said collector during weight accretion and wherein said tubing isolates said collector from said conveying means to eliminate any apparent weight change of said collector that would otherwise be imposed by forces associated with said conveying means due to relative movement between said collector and said conveying means.

17. The apparatus as set forth in claim 16 wherein any forces imposed by said tubing upon said collector during flexing of said tubing as a result of the repositioning of said collector during collection of the volatile fluid of interest create an apparent weight change of said collector which weight change is insignificant relative to the weight of the volatile fluid of interest that is collected.

18. A method for determining the percent of weight of a fluid of interest in a test sample of known weight, said method comprising the steps of:
(a) heating the test sample within a chamber to convert the volatile fluid of interest to a gaseous state;
(b) conveying the gaseous volatile fluid of interest from the chamber to a collector;
(c) collecting the gaseous volatile fluid of interest in the collector;
(d) determining the change in weight of the collector in response to collection of the gaseous volatile fluid of interest by supporting the collector on an electromagnetic force balance while the collector is in fluid communication with the chamber and while the gaseous fluid of interest is conveyed from said chamber to said collector;
(e) comparing the change in weight of the collector with the weight of the test sample to determine the percent by weight of the fluid of interest in the test sample; and
(f) isolating the collector from the imposition of any forces due to movement of the collector relative to the chamber during the accretion of weight by the collector.

19. The method as set forth in claim 18 including the step of isolating the collector against transmission of any mechanically imposed forces arising from the carrying out of said step of conveying.

20. The method as set forth in claim 19 including the step of computing the change in weight of the collector resulting from the collection of the volatile fluid of interest from the test sample.

21. The method as set forth in claim 18 including the step of transporting the sample into and out of the chamber.

22. The method as set forth in claim 21 including the step of repositioning a magnet to carry out said step of transporting by exerting a magnetic force to transport the sample.

23. The method as set forth in claim 18 wherein the volatile fluid of interest is water and wherein said step of collecting includes the step of absorbing the water with a desiccant.

24. The method as set forth in claim 18 including the step of urging the flow of the gaseous volatile fluid of interest from the chamber to the collector.

25. The method as set forth in claim 18 including the step of purging the chamber and the collector of the gaseous volatile fluid of interest prior to exercise of said step of heating.

26. Apparatus for determining by weight the amount of volatile fluid of interest in a sample under test, said apparatus comprising in combination:
(a) a closed compartment for housing the sample;
(b) means for heating the sample in said compartment to convert the volatile fluid of interest into a gaseous state;
(c) means for collecting the volatile fluid of interest;
(d) means for interconnecting said compartment with said collecting means in fluid communication with one another;
(e) means for urging flow of the volatile fluid of interest in a gaseous state from said compartment to said collecting means;
(f) means for determining the change in weight of said collecting means resulting from the collection of the volatile fluid of interest while said collecting means is in fluid communication with said compartment and during flow of the volatile fluid of interest to said collecting means by repetitively vertically repositioning said collecting means commensurate with the weight accretion of said collecting means; and
(g) means for isolating said collecting means from any forces which would be imposed by said interconnecting means upon said collecting means as a result of vertical repositioning of said collecting means relative to said interconnecting means during flow of the volatile fluid of interest through said interconnection means and said collecting means during operation of said determining means.

27. The apparatus as set forth in claim 25 including means for purging said compartment, said interconnecting means and said collecting means of the volatile fluid of interest prior to housing the sample in said compartment.

28. The apparatus as set forth in claim 26 wherein the volatile fluid of interest is water and wherein said collecting means includes a desiccant and wherein said urging means includes flow of a dry gas.

29. The apparatus as set forth in claim 26 including means for purging said compartment, said interconnecting means and said collecting means of the volatile fluid of interest prior to housing the sample in said compartment.

30. The apparatus as set forth in claim 29 wherein said purging means includes a pump for pumping a dry gas into said compartment.

31. The apparatus as set forth in claim 30 wherein said pump is an air pump and including means for removing any water in the air pumped by said air pump.

32. The apparatus as set forth in claim 26 wherein said determining means comprises an electromagnetic force restoration balance which periodically vertically repositions said collecting means.

33. The apparatus as set forth in claim 32 wherein said isolating means includes a length of flexible tubing to prevent imposition of more than negligible forces upon said collecting means during vertical movement of said collecting means whereby, flexing of said tubing will not result in an apparent weight change of said collecting means and said determining means will not sense the flexing of said tubing.

34. The apparatus as set forth in claim 33 including means for transporting the sample into and out of said compartment.

35. The apparatus as set forth in claim 34 wherein said transporting means includes a magnet, means for relocating said magnet and means responsive to the magnetic field of said magnet for obtaining transport of the sample in response to the relocated magnetic field resulting from relocating said magnet.

36. The apparatus as set forth in claim 33 wherein said collecting means includes means for forcing upward vertical flow of the volatile fluid of interest through said collecting means.

37. The apparatus as set forth in claim 36 wherein said collecting means includes on inlet disposed proximate the lower end of said collecting means, said inlet being connectible to said length of tubing and an outlet disposed proximate the upper end of said collecting means.

38. The apparatus as set forth in claim 26 including means for transporting the sample into and out of said compartment.

39. The apparatus as set forth in claim 38 wherein said transporting means includes a magnet, means for relocating said magnet and means responsive to the magnetic field of said magnet for obtaining transport of the sample in response to the relocated magnetic field resulting from relocating said magnet.

40. The apparatus as set forth in claim 26 wherein said collecting means includes means for forcing upward vertical flow of the volatile fluid of interest through said collecting means.

41. The apparatus as set forth in claim 40 wherein said collecting means includes an inlet disposed proximate the lower end of said collecting means, said inlet being connectible to said interconnecting means and an outlet disposed proximate the upper end of said collecting means.

42. Apparatus for collecting and weighing a volatile fluid of interest from a sample under test, said apparatus comprising in combination:
(a) an oven for heating the sample under test and converting the volatile fluid of interest to a gaseous state;
(b) a collector for collecting the volatile fluid of interest;
(c) means for conveying flow of the volatile fluid of interest from said oven to said collector;
(d) means for determining the change in weight of said collector in response to the collection of the volatile fluid of interest, said determining means including means for supporting said collector during weight accretion and for accommodating repetitive downward movement of said collector in response to the weight accretion and means for repetitively repositioning said collector upwardly after each downward movement; and
(e) said conveying means including a length of flexible tubing for isolating said collector against any apparent weight change, that would be sensed by said determining means due to relative movement between said collector and said conveying means.

43. Apparatus for collecting and weighing a volatile fluid of interest from a sample under test, said apparatus comprising in combination:
(a) an oven for heating the sample under test and converting the volatile fluid of interest to a gaseous state;
(b) means for conveying flow of the gaseous volatile fluid of interest from said oven;
(c) a collector for collecting the gaseous volatile fluid of interest;

(d) means for interconnecting said conveying means with said collector;
(e) said interconnecting means including means for isolating said collector from said conveying means to eliminate any apparent weight change imposed by forces associated with said interconnecting means due to relative movement between said collector and said conveying means; and
(f) means responsive to a weight increase of said collector due to accretion of the fluid of interest therein for positionally moving said collector relative to said conveying means and for determining the change in weight of said collector as a result of such movement during collection of the volatile fluid of interest.

44. Apparatus for collecting and weighing a volatile fluid of interest from a sample under test, said apparatus comprising in combination:
    (a) an oven for heating the sample under test and converting at least the volatile fluid of interest to a gaseous product;
    (b) means for conveying gaseous products, including the volatile fluid of interest, from said oven to a location remote from said oven;
    (c) a collector for receiving the gaseous products and for collecting and accumulating the volatile fluid of interest, said collector increasing in weight in response to the quantity of the volatile fluid of interest collected, said collection including an inlet in fluid communication with said conveying means for receiving the gaseous products and an outlet for discharging the gaseous products received by said collector and not collected by said collector;
    (d) means responsive to the weight of said collector for determining the change in weight of said collector simultaneously with accumulation of the volatile fluid of interest within said collector during flow of the volatile fluid of interest into said collector;
    (e) means for removably supporting said collector upon said weight determining means; and
    (f) means for isolating said collector from imposition of any forces due to relative vertical movement between said collector and said conveying means while the volatile fluid of interest is being collected.

45. Apparatus for collecting and weighing a volatile fluid of interest from a sample under test, said apparatus comprising in combination:
    (a) an oven for heating the sample under test and converting the volatile fluid of interest to a gaseous state;
    (b) a collector having an inlet for collecting the volatile fluid of interest;
    (c) an electromagnetic force restoration balance for determining the change in weight of said collector in response to collection of the volatile fluid of interest by repetitively restoring the position of said collector during weight accretion and for sensing the cumulative forces necessary for restoration; and
    (d) means for conveying the flow of the volatile fluid of interest from said oven to said collector, said conveying means including a length of flexible tubing connected to said inlet, said length of tubing being sufficiently limp to avoid imposing any apparent weight change of said collector due to flexing of said tubing during repositioning of said collector by said electromagnetic force restoration balance.

* * * * *